Figure 1:
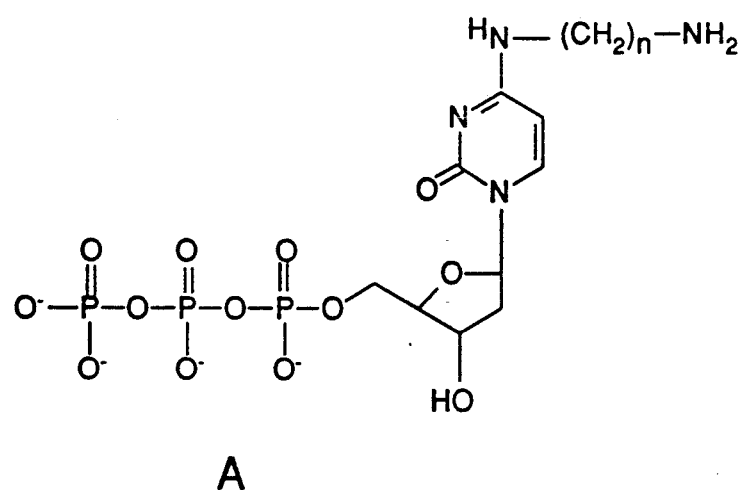
Figure 1:
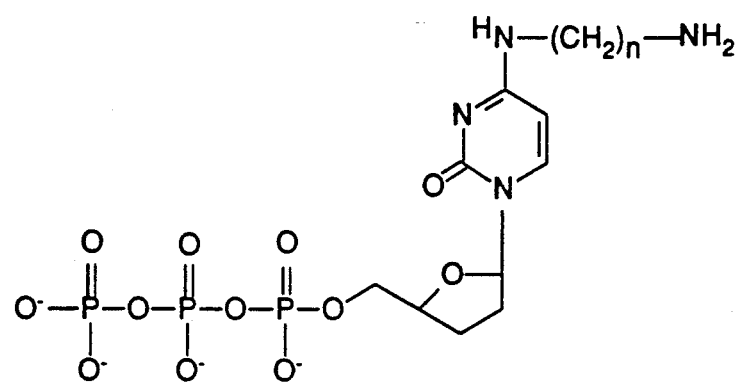

United States Patent [19]
Cruickshank

[11] Patent Number: 5,091,519
[45] Date of Patent: Feb. 25, 1992

[54] NUCLEOTIDE COMPOSITIONS WITH LINKING GROUPS

[75] Inventor: Kenneth Cruickshank, Lisle, Ill.

[73] Assignee: Amoco Corporation, Chicago, Ill.

[21] Appl. No.: 858,600

[22] Filed: May 1, 1986

[51] Int. Cl.⁵ .............................................. C07H 19/00
[52] U.S. Cl. .................................... 536/29; 536/23; 536/26
[58] Field of Search ........................... 536/23, 29

[56] References Cited
U.S. PATENT DOCUMENTS

| 4,458,066 | 7/1984 | Caruthers et al. | 536/27 |
| 4,699,876 | 10/1987 | Libeskind | 536/27 |
| 4,910,300 | 3/1990 | Urdea et al. | 536/26 |

FOREIGN PATENT DOCUMENTS

| 0063879 | 11/1982 | European Pat. Off. | 536/23 |
| 083063053 | 8/1989 | European Pat. Off. | |
| 8602929 | 5/1986 | PCT Int'l Appl. | 536/29 |
| 8606726 | 11/1986 | PCT Int'l Appl. | 536/29 |

Primary Examiner—John W. Rollins
Assistant Examiner—James O. Wilson
Attorney, Agent, or Firm—Norville Galloway; William H. Magidson; Ralph C. Medhurst

[57] ABSTRACT

The present invention includes nucleotide compositions having linking groups and the use and manner of making the nucleotide compositions. The nucleotide compositions are used to attach nonisotopic label moieties to nucleic acid probes.

4 Claims, 5 Drawing Sheets

A

B

A

B (lysine)

(serine)

(glycyl-glycine)

(cystine)

(cystamine)

(glycine)

TTTTC*TTT

TTTTC*TTT

NUCLEOTIDE COMPOSITIONS WITH LINKING GROUPS

BACKGROUND OF THE INVENTION

The present invention pertains to compositions and methods for the use and synthesis of the compositions. The present invention includes modified nucleotide compositions having linking groups capable of associating with label moieties.

The following definitions are provided to facilitate an understanding of the present invention. The term "probe" refers to a ligand of known qualities capable of selectively binding to a target antiligand. As applied to nucleic acids, the term "probe" refers to a strand of nucleic acid having a base sequence complementary to a target strand.

The term "linking group" is used broadly to denote a hydrocarbon moiety capable of reacting with a nucleotide or nucleotide derivative and another compound.

The term "label" refers to a molecular moiety capable of detection including, by way of example, without limitation, radioactive isotopes, enzymes, luminescent agents, and dyes. The term "agent" is used in a broad sense, including any molecular moiety which participates in reactions which lead to a detectable response. The term "cofactor" is used broadly to include any molecular moiety which participates in reactions with the agent.

Genetic information is stored in living cells in thread-like molecules of DNA. In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenosine in an opposing complementary strand.

DNA consists of covalently linked chains of deoxyribonucleotides and RNA consists of covalently linked chains of ribonucleotides. The genetic code of a living organism is carried upon the DNA strand in the sequence of the base pairs.

Each nucleic acid is linked by a phosphodiester bridge between the five prime hydroxyl group of the sugar of one nucleotide and the three prime hydroxyl group of the sugar of an adjacent nucleotide. Each linear strand of naturally occurring DNA or RNA has one terminal end having a free five prime hydroxyl group and another terminal end having a three prime hydroxyl group. The terminal ends of polynucleotides are often referred to as being five prime termini or three prime termini in reference to the respective free hydroxyl group. Complementary strands of DNA and RNA form antiparallel complexes in which the three prime terminal end of one strand is oriented and bound to the five prime terminal end of the opposing strand.

Nucleic acid hybridization assays are based on the tendency of two nucleic acid strands to pair at complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences or specific genes within the total DNA or RNA extracted from tissue or culture samples, may indicate the presence of physiological or pathological conditions. In particular, the identification of unique DNA or RNA sequences or specific genes, within the total DNA or RNA extracted from human or animal tissue may indicate the presence of genetic diseases or conditions such as sickle cell anemia, tissue compatibility, cancer and precancerous states, or bacterial or viral infections. The identification of unique DNA or RNA sequences or specific genes within the total DNA or RNA extracted from bacteria, bacterial cultures or tissue containing bacteria may indicate the presence of antibiotic resistance, toxins, viruses, or plasmids, or provide identification between types of bacteria.

Thus, nucleic acid hybridization assays have great potential in the diagnosis and detection of disease. Further potential exist in agriculture and food processing where nucleic acid hybridization assays may be used to detect plant pathogenesis or toxin producing bacteria.

One of the most widely used nucleic acid hybridization assay procedures is known as the Southern blot filter hybridization method or simply, the Southern procedure (Southern, E., *J. Mol. Biol. I*, 98,503, (1975). The Southern procedure is used to identify target DNA or RNA sequences. This procedure is generally carried out by immobilizing sample RNA or DNA to nitrocellulose sheets. The immobilized sample RNA or DNA is contacted with radio-labeled o—labeled probe strands of DNA having a base sequence complementary to the target sequence carrying a radioactive moiety which can be detected. Hybridization between the probe and the sample DNA is allowed to take place.

The hybridization process is generally very specific. The labeled probe will not combine with sample DNA or RNA if the two nucleotide entities do not share substantial complementary base pair organization. Hybridization can take from three to 48 hours depending on given conditions.

Unhybridized DNA probe is subsequently washed away. The nitrocellulose sheet is placed on a sheet of X-ray film and allowed to expose. The X-ray film is developed with the exposed areas of the film identifying DNA fragments which have been hybridized to the DNA probe and therefore have base pair sequence of interest.

The use of radioactive labeling agents in conjunction with Southern assay techniques have allowed the application of nucleic acid assays to clinical samples. However, the use of radioactive labeling techniques requires a long exposure time to visualize bands on X-ray film. A typical Southern procedure may require 1 to 7 days for exposure. The use of radioactive labeling agents further requires special laboratory procedures and licenses.

The above problems associated with assays involving radioisotopic labels have led to the development of techniques employing nonisotopic labels. Examples of nonisotopic labels include enzymes, luminescent agents, and dyes. Luminescent labels emit light upon exitation by an external energy source and may be grouped into categories dependent upon the source of the exciting energy, including: radioluminescent labels deriving energy from high energy particles; chemiluminescent labels which obtain energy from chemical reactions; bioluminescent labels wherein the exciting energy is applied in a biological system; and photoluminescent or fluorescent labels which are excitable by units of electromagnetic radiation (photons) of infrared, visable, or ultraviolet light. See, generally, Smith et al., *Ann Clin. Biochem.*, 18: 253, 274 (1981).

Nonisotopic assay techniques employing labels excitable by nonradioactive energy sources avoid the health hazards and licensing problems encountered with radioisotopic label assay techniques. Moreover, nonisotopic assay techniques hold promise for rapid detection avoiding the long exposure time associated with the use of X-ray film.

However, nonradioisotopic assays have not conveyed the sensitivity or specificity required of assays intended for the clinical market. In part, the problem lies in associating a label to a probe without interferring with the hybridization process. A further problem includes the associating of a label to a probe without interferring with the performance of the label.

DNA, unlike proteins, does not contain a variety of organic functional groups which are amenable to direct chemical labeling. An essential pre-requisite therefore to the preparation of non-radioisotopically labeled DNA probes is the chemical manipulation of DNA either at the poly or mononucleotide level such that suitable functionality becomes available for label attachment. Several synthetic methods are described in the literature which enable labeling of DNA with various label groups, for example, Biotinylation: Langer, P. R., Waldrop, A. A. and Ward, D. C. Proc. Nat'l. Acad. Sci. U.S.A. 78(11), 6633, 1981; Kempe, T., Sundquist, W. I., Chow, F. and Hu, S-L., Nucl. Acid. Res. 13(1), 45, 1985; Aliphatic amine group attachment: Chu, B. C. F., Wahl, G. M. and Orgel, L. E., Nucl. Acid. Res. (18), 6513, 1983; Dreyer, G. B. and Dervan P. B., Proc. Nat'l. Acad. Sci. U.S.A., 82, 968, 1985; Sulfhydryl group attachment: Eshaghpour, H., Soll, D. and Crothers, D. M., Nuc'l. Acid. Res., 7(6), 1485, 1979; and Conolly, B. A. and Rider, P., Nucl. Acid. Res. 13 (12), 4485, 1985. However, the synthetic techniques described in the literature involve complex multistage procedures which employ toxic and/or expensive heavy metal reagents.

DESCRIPTION OF THE INVENTION

The present invention presents compositions and methods for using and making the compositions for labeling nucleic acid probes. One nucleotide composition includes a nucleotide triphosphate having a linking group carried on an exocyclic functional group of the base, which can be added to the 3'-termini of probe sequences using enzymes. A further nucleotide composition includes a nucleotide reactive phosphorus derivative, having a linking group carried on an exocyclic functional group of the base which can be located at any desired position within a DNA probe sequence using known DNA synthesis methods.

The linking group can carry functional groups which can react with label moieties for non-radioisotopic detection of DNA probes. The linking group may include aliphatic chains, substituted aliphatic chains, cyclic moieties, amino acids and derivatives thereof. As used herein, an exocyclic functional group includes carbonyl groups or amine groups of a nucleotide base.

Turning now to the nucleotide triphosphate composition in greater detail, an embodiment of the present invention includes a nucleotide triphosphate composition wherein the nucleotide base is pyrimidine derivatives having a linking group carried on an exocyclic primary amine. Cytosine contains an exocyclic amine at the $N^4$ position. Other bases can be modified to convert carbonyl functional groups to amines.

Preferably the linking group includes a carbon chain of between 3 to 9 carbons in length. However, individuals skilled in the art may vary the chain of carbon as needed for a particular application.

A preferred embodiment includes a linking group having a functional group which can be reacted under mild conditions with label moieties. A preferred functional group includes amines which react with amine reactive label moieties. As used herein, the term "amine reactive" refers to features or functional groups of a compound that will react with an amine group on a second compound.

Triphosphate forms of the present invention are suitable for incorporation into oligonucleotides enzymatically. Thus, the enzyme terminal deoxynucleotidyl transferase (TDT) can be used to add nucleotide triphosphates having aliphatic carbon chains to the 3'-termini of probe sequences.

A further composition includes a reactive phosphorus derivative of a nucleotide having a linking group carried on an exocyclic functional group. As used herein, the term reactive phosphorus means able to undergo reactions under mild conditions. An example without limitation includes phosphoramidite derivatives.

A further embodiment of the present invention includes a method of labeling a polynucleotide probe comprising the steps of incorporating a nucleotide, having a cytosine base or derivative thereof, having a linking group carried on the exocyclic primary amine, into an oliogonucleotide. Next, the method includes reacting the linking group with a label moiety.

A preferred embodiment includes a linking group which includes functionality capable of reacting with a label moiety under mild conditions. Suitable functional group includes by way of examples without limitation amines, carboxylic acids, alcohols and thiol groups.

Incorporation of the nucleotide into an oligonucleotide may be accomplished with a reactive phosphorus derivative of the modified nucleotide which can be incorporated into an oligonucleotide by standard chemistry including automated DNA synthesis equipment. Alternatively, incorporation of the modified nucleotide can be accomplished using a triphosphate derivative of the modified nucleotide and the enzyme terminal deoxynucleotidyl transferase, DNA polymerase and other.

A still further embodiment of the present invention includes a method of making a nucleotide having a linking group carried on the exocyclic primary amine group. One method includes reacting a nucleotide with an exocyclic primary amine group with an aliphatic amine in a bisulfite reaction solution. A further method includes reacting a derivative of a nucleotide, having a blocking group such as dimethoxytrityl, at an exocyclic functionality having a leaving group reactive with nucleophiles under mild conditions to form a reaction product. As used herein, mild conditions are conditions which do not denature proteins. Generally, mild conditions include a temperature not exceeding about 40° C. and a substantially neutral pH.

Preferred embodiments of the method including leaving groups such as, by way of example without limitation, nitrogen substituted cyclic compounds, halogens and oxygenated phenyl groups. A preferred leaving group includes 1, 2, 4-triazole. A preferred nucleophile includes $N^1$-trifluoroacetyl-1,6-hexanediamine.

The nucleotide bases guanine, thymine and uracil have exocyclic carbonyl groups which react with preferred leaving groups. Substitution at the four position of the uracil base with an aliphatic amine forms a cytosine phosphoramidite derivative.

The methods and compositions of the present invention permit the bonding of label groups from small luminescent compounds to large proteins to nucleic acids. The procedure is compatible with the labeling of oligomers or large strands of nucleic acid. The method and compositions are compatible with enzymatic incorporation into nucleic acids or employ standard chemical reactions permitting automated DNA or RNA synthesis using the modified nucleotides. The present invention is further described in the following experimental examples which exemplify features of the preferred embodiments. The experimental protocol sets forth typical conditions and procedures.

EXPERIMENTAL EXAMPLES

I. Synthesis

A. General Methods and Materials

All chemicals were of analytical grade and used as available from manufacturers or distributors unless otherwise indicated.

Thin-layer chromatography (TLC) was performed on Merck silica gel 60F-254 glass-backed plates. The following solvent systems were used: solvent system A, chloroform-methanol (19:1,v/v); solvent system B chloroform-methanol (9:1,v/v); solvent system C, chloroform-methanol (4:1,v/v). After development, substances were detected by UV light.

B. Preparation of $N^4$-(3-Aminopropyl)-2'-deoxycytidine-5'-triphosphate

The bisulfite reaction mixture was freshly prepared as follows: A solution of 1,3-propanediamine (0.740 g. 10.0 mmole) in water was adjusted to pH 7.08–7.12 by addition of solid sodium metabisulfite (ca. 2.35g are required) and the final volume was adjusted to 10 ml.

Deoxycytidine triphosphate (dCTP) (100 mgs) was added to 10 ml of the bisulfite reaction solution and the mixture was incubated at 37° C. for seven days in a tightly sealed vessel. The pH of the reaction solution was maintained at pH 7.1 by addition of small amounts of sodium metabisulfite. The progress of the reaction was monitored by high pressure liquid chromotography (HPLC). This system clearly showed the progressive disappearance of dCTP to give one new nucleotide triphosphate component. To isolate the product, the reaction mixture was diluted to a volume of 2.75 l with deionized water and applied to a column of DEAE Sephadex A-25 (2.6×68/70 cm). Elution with a linear gradient of triethylammonium bicarbonate buffer (pH 7.8, 0.05–0.6M) and subsequent lyophilization of the appropriate fractions yielded $N^4$-(3-aminopropyl)-2'-deoxycytidine-5'-triphosphate triethylammonium salt AP-dCTP (8.6 mmol. 86% yield) as an amorphous powder. The structure of AP-dCTP is depicted in FIG. 1 as A wherein N equals 3. The substance was homogeneous by HPLC ($R_T$ 18.5 min. IBM AMINO column S.N. 4112202, modified in-house by methylation with MeI). The mobile phase consisted of an initial buffer of 0.05M $KH_2PO_4$ in MeOH—$H_2O$ (3:7, v/v) to which was added (1% min$^{-1}$) the same buffer supplemented with 1M $(NH_4)_2SO_4$. Deoxyuridine triphosphate and dCTP had $R_T$ 17.6 and 19.4 respectively in this system.

The substance was further charactorized by the following features: $^1H$ NMR(200 MHz, DSS), ($D_2O$) 7.89(d, J=7.6 Hz, 1H, H-6), 6.34(t, J=7.0 Hz, 1H, H-1'), 6.12(d, J=7.6 Hz, 1H, H-5), 4.60 (shoulders on HDO peak), 4.21 (d, J=4.2 Hz§, 2H), 3.51 (m, 2H), 3.06(m, 2H), 2.37(m, 2H), 1.97(m, 2H). UV ($H_2O$) lambda$_{max}$272.5 nm. $^{31}P$ NMR ($D_2O$), trimethylphosphate=0)−11.9 m, −14.0 d, −25.3 m. The substance gave a positive ninhydrin test.

C. $N^4$-(3-Aminopropyl)-2',3'-dideoxycytidine-5'-triphosphate (3).

2',3'-dideoxycytidine-5'-triphosphate (20 umol) was dissolved in 1.0 ml of the 1,3-propanediamine/bisulfite reaction mixture and incubated at 37° C. for 60 hr. when HPLC indicated complete conversion of the starting material to one new major substance. The product was isolated by Sephadex chromatography and lyophilization in the manner described above to yield 16.0 umol (80%) of an amorphous solid and identified as $N^4$-(3-aminopropyl)-2'3'-dideoxycytidine-5-triphosphate AP-ddCTP. The structure of AP-ddCTP is depicted in FIG. 1 as B where N equals three. The solid was homogeneous by HPLC (RT=20.02 min, RT(ddCTP)=21.08) and characterized by UV lambda max ($H2O$)=272.5 nm.

D. 2'-Deoxycytidine-5'-triphosphate/Amine reactive conjugates

Figure 2:
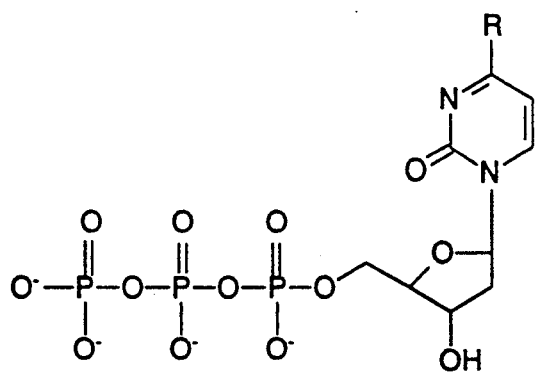
Figure 2:
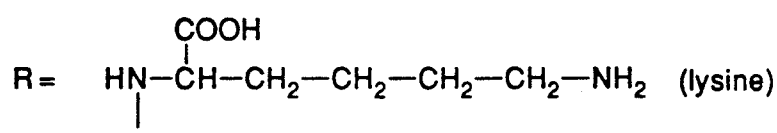
Figure 2:
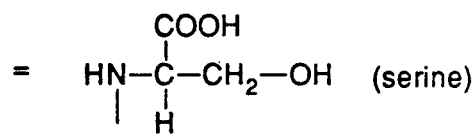
Figure 2:
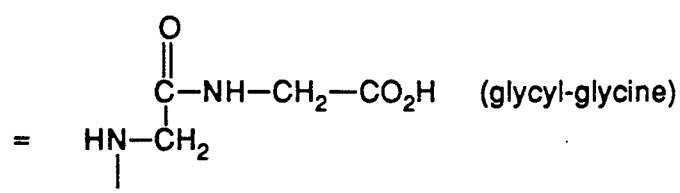
Figure 2:
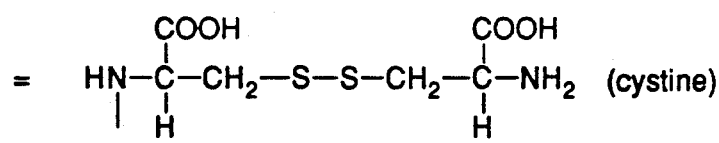
Figure 2:
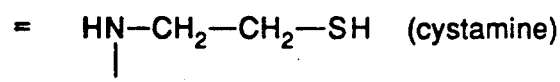
Figure 2:
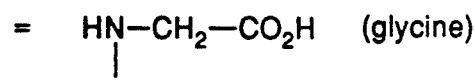

Conjugates of 2'-deoxycytidine-5'-triphosphate were prepared by dissolving dCTP (10 mgs/ml) in a reaction mixture containing 2M bisulfite at pH 7.05–7.01 and which contained saturating amounts of amine reactive compounds. The amine reactive compounds included the cystamine and the amino acids glycine, cystine, lysine and serine. The reaction mixtures were prepared by adding a saturating quantity of the amine reactive compound to a 2M bisulfite solution and adjusting the pH by addition of solid lithium hydroxide. The reaction mixtures were monitored by HPLC and an the appropriate time the products were isolated in the manner described in previous sections including dilution in deionized water, application to a Sephadex column, elution with a triethylammonium bicarbonate buffer and lyophilization. The reaction products are depicted in FIG. 2 generally designated as C wherein R equals various reactive amines including lysine, serine, glycine, glycyl-glycine, cystine and cystamine.

Figure 3:
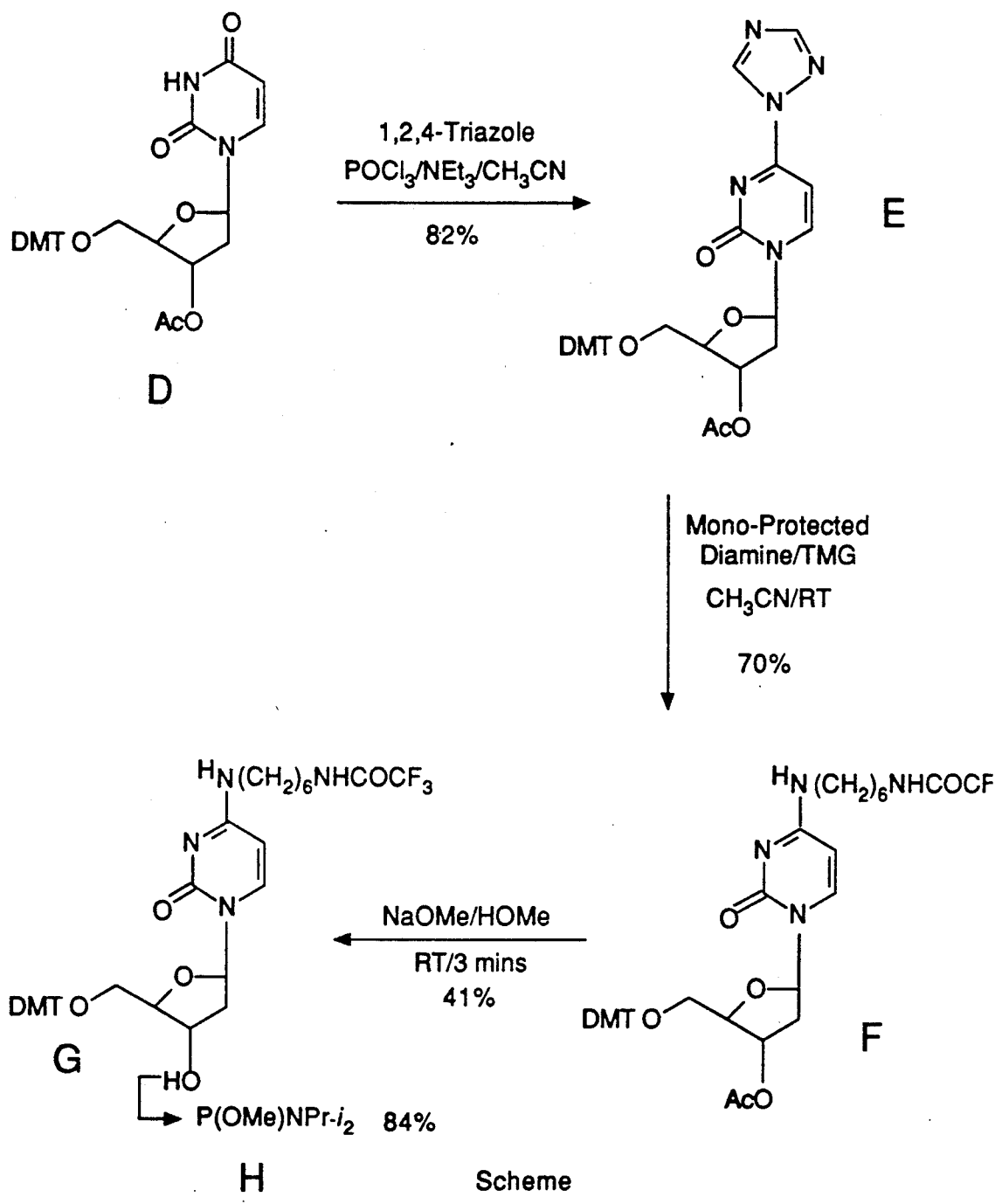

E. Synthetic Route To Phosphoramidite 1. 4-(1,2,4-Triazol-1-yl)-1-(β-D-5'-Dimethoxytrityl-3'-acetyl)ribofuranosyl) pyrimidin-2(1H)-one Turning now to FIG. 3, to a cooled magnetically stirred solution of phosphorus oxychloride (5.73 g, 37.4 mmol) in dry acetonitrile (100 ml) was added 1,2,4-triazole (11.62 g, 160.8 mmol) followed by triethylamine (16.24 g, 160.8 mmol). To this mixture was added a solution of 5'-dimethoxytrityl-3'-acetyl-2'-deoxyuridine (10.72 g, 18.7 mmol) represented in FIG. 3 as D, in dry acetonitrile (60 ml) in portions over 10 minutes. The resulting mixture was stirred at room temperature for four hours when TLC indicated complete conversion of the starting material to one new product. The reaction was quenched by addition of a mixture of triethylamine (14 ml) and water (4 ml), stirred for a further 10 minutes, then evaporated in vacuo. The residue was dissolved in chloroform (200 ml), extracted with saturated NaHCO₃ solution (200 ml), dried (MgSO₄) and evaporated to an oil to yield 10.02 g (86%) 4-(1,2,4-triazol-1-yl)-1-(β-D-5'-Dimethoxytrityl)-3'-acetyl)-ribofuranosyl)pyrimidin-2(1H)-one.

2.
N⁴-(6-N-Trifluoroacetylaminohexyl)-5'-Dimethoxytrityl-3'-Acetyl-2'-Deoxycytidine The fore-going triazolo-nucleoside (E) (10.63 g, 17 mmol), N¹-trifluoroacetyl-1,6-hexanediamine hydrochloride (5.57 g, 20.4 mmol) and N¹,N¹,N³,N³-tetramethylguanidine (3.52 g, 30.6 mmol) in dry acetonitrile (100 ml) was stirred at room temperature for four hours when TLC indicated complete conversion of starting material to one major new lower $R_f$ substance. The solvent was evaporated in vacuo, the residue dissolved in chloroform (150 ml), extracted with saturated. NaHCO₃ solution, dried (MgSO₄) and evaporated to an oil which was further purified by flash chromatography as descried by Still. W. C., Kahn, M. and Mitra, A. *J. Org. Chem.*, 43(14) 2923,1978. Reactions and recovery produced a yield of 9.39 g (70%). N⁴-(6-N-trifluoroacetyl aminohexyl)-5'-dimethoxytrityl-3'-acetyl-2'-deoxycytidine, identified in FIG. 3 as F and hereinafter referred to as TFAAH-DMT-Acetyl-dC.

3.
N⁴-(6-N-Trifluoroacetylaminohexyl)-5'-Dimethoxytrityl-2'-Deoxycytidine

TFAAH-DMT-Acetyl-dC (9.0 g, 11.35 mmol) was dissolved in methanol (235 ml) and sodium methoxide in methanol (39 ml of a 1.1M soln) was added to the stirred solution. After 2 minutes at room temperature a cation exchange resin, such as Dowex 50X2-100, (100 g, pyridinium form) was added. Following the addition of Dowex 50X2-100 the pH of the reaction mixture was 6.5. The resin was removed by filtration, washed with methanol (50 ml) and the combined filtrates evaporated to near 50 ml in vacuo. Chloroform (200 ml) was added to the residue, the mixture transferred to a separating funnel and washed with saturated. NcHCO₃ solution (200 ml). The organic layer was separated and evaporated to a pale-yellow oil which was further purified by flash chromatography to yield (3.5 g, 41%) of a pale-yellow foam, homogeneous by TLC (System B). The substance was identified as N⁴-(6-N-trifluoroacetyl aminohexyl)-5'-dimethoxytrityl-2'-deoxycytidine identified in FIG. 3 as G and referred to hereinafter as TFAAH-DMT-dc. TFAAH-DMT-dc was further characterized by the following features:

¹H NMR (CDCl₃): 7.79 (d,1H,J=7.8 Hz, H-6), 7.43–7.25 (m), 6.86–6.80 (m),.6.30 (m, 1H, H-1'), 5.34 (d, 1H, J=7.8 Hz, H-5), 5.09 (m, 1H), 4.49 (m, 1H, H-3'), 4.03 (m, 1H, H-4'), 3.79 (s,6H), 3.49–3.32 (m, 2H,H-5', H-5"), 2.64 (m, 1H, H-2), 2.51 (m, 1H, H-2'), 1.7–1.3 (m br, alkyl).

4.
N⁴-(6-N-Trifluoroacetylaminohexyl)-5'-Dimethoxytrityl-2'-Deoxycytidine-3'-(Methyl-N, N-Diisopropyl)phosphoramidite TFAAH-DMT-dc G was converted to the phosphoramidite essentially by the procedure described by McBridge, L. J. and Caruthers, M. H., Tet Let, 24, (3) 245, (1983) except that after extraction with saturated NaHCO₃ solution, the ethyl acetate layer was evaporated and the residue purified by flash chromatography. Elution with ethyl acetate-triethylamine 9.73 vol/vol. produced a yield of 82% of N⁴-(6-N-trifluoroacetylaminohexyl)-5'-dimethoxytrityl-2'-deoxycytidine-3'-(methyl-N,N-iisopropyl)phosphoramidite identified in FIG. 3 as H and hereinafter referred to as TFAAH-DMT-dc-phosphoramidite.

The phosphoramidite compound described above is compatible with automated DNA synthesis equipment based on phosphoramidite chemistry including equipment marketed by Applied Biosystems under the mark and identification 380 B DNA Synthesizer. TFAAH-DMT-dc-phosphoramidite was used in an Applied Biosystems synthesizer using standard procedures and nucleotide phosphoramidite intermediates, reagents and solvents supplied by the manufacturer. The following oligonucleotides were synthesized wherein C* signifies the modified cytidine derivative:

5'AAAAAAC*T3'
5'TTTTC*TTT3'
5'TTTTTTC*TTTTTT3'
5'TGGAC*C-ATT 3'.

The analysis of crude synthetic DNA was carried out on an ion-exchange HPLC in a manner described previously.

The efficiency of each coupling step was assayed colorimetrically using the characteristic absorbance of the dimethoxytrityl cation. After removal from the support the crude synthetic DNA oligomer was analyzed by ion-exchange HPLC. To assay for the presence of a primary amino-function within the DNA sequence, a sample of the crude oligomer, 5'-TTTTC*TTT-3', was reacted in solution with an excess of an N-hydroxysuccinimide active ester of a biotin derivative.

Figure 4A:
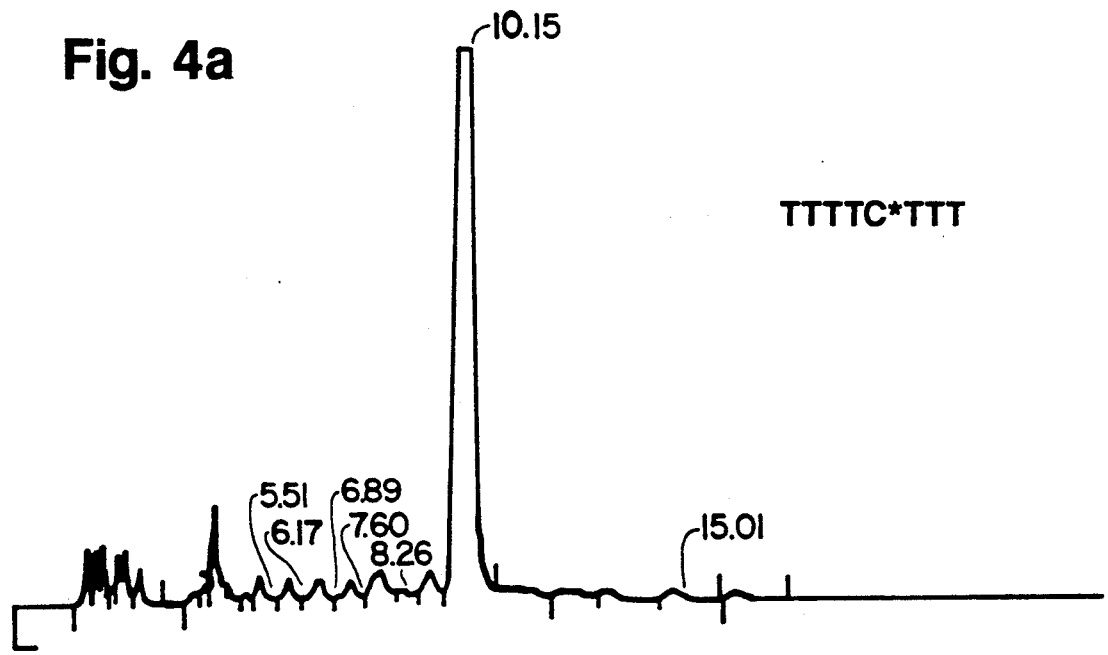
Figure 4B:
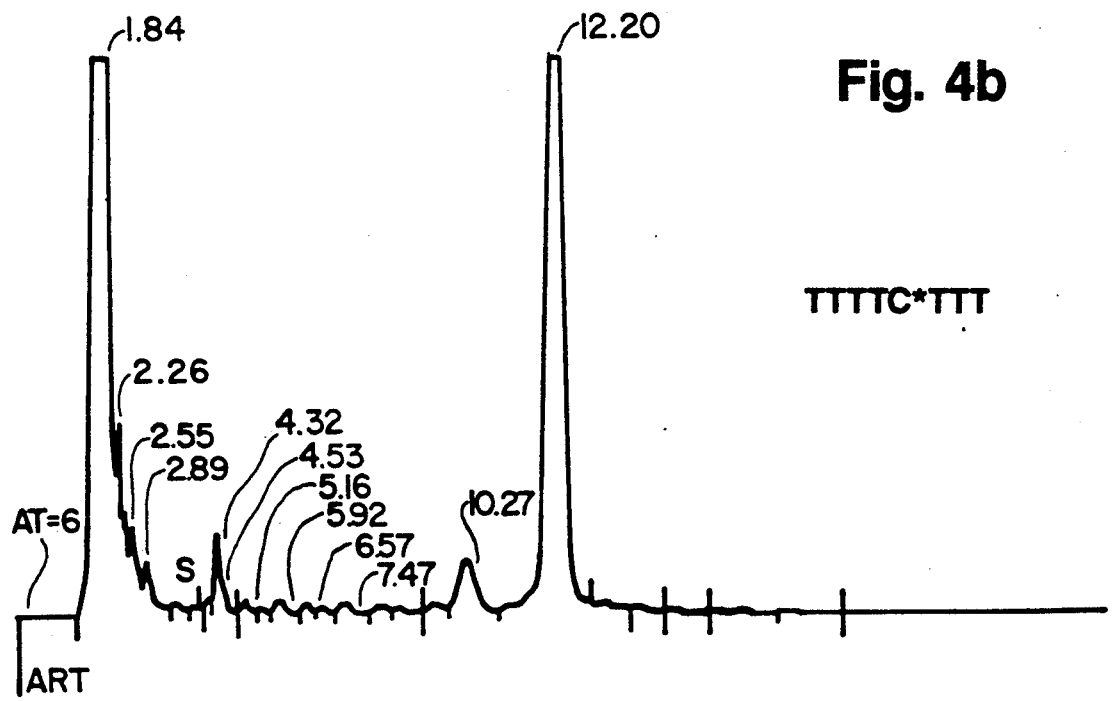

The oligonucleotide (5 O.D. units) was dissolved in 0.1M sodium borate buffer (pH 8.0, 0.5 ml) and a solution of biotinyl-6-aminocaproic acid N-hydroxysuccinimide ester (Calbiochem. 5 mg) in DMF (50 ul) was added. The mixture was stored at room temperature for 1-2 hours when HPLC analysis showed the reaction to be complete. In all cases the synthetic DNA underwent a clean, efficient conversion to a new substance on HPLC. Moreover, the changes in retention time were consistent with the conversion of a primary-amino group into an amide linkage. FIG. 4 shows a) an HPCL chromatogram of crude TTTTC*TTT octamer and b) an HPLC analysis of the crude reaction mixture formed after reaction with an active NHS-ester.

II. Incorporation into Probes and Detection

A. Materials and Methods

B-phycoerythrin, fluorescein-5-isothiocyanate, eosin-5-isothiocyanate, and N-hydroxysuccinimidyl 1-pyrenebutanoic acid were obtained from Molecular Probes (Junction City, Oreg.) DNA homopolymer, cellulose-immobilized oligomers, and gel permeation chromatography media were obtained from Pharmacia (Piscataway, N.J.).

B. Preparation of 3'-labeled DNA

The 3' termini of single stranded DNA were labeled in two reaction steps. For multiple labeling of oligomers, the enzyme terminal deoxynucleotidyl transferase (tdt) was used to sequentially attached modified deoxynucleotide triphosphates to the 3'-hydroxyl terminal of individual DNA oligomers. This process is referred to as "tailing" since an oligomer is produced which contains a 3' "tail" of modified bases. The modified bases in experiments reported here possess aliphatic amine substituents which allow further modification by reaction with amine reactive fluoropores or chemiluminescent compounds. The modified nucleoside triphosphates employed in the tailing reactions were $n^4$-(3-aminopropyl)-2'-deoxycytidine-5'-triphosphate (APdCTP). The following procedure is typical. Eight nanomole of DNA, containing terminal 3'-hydroxyl groups, was transferred to a conical plastic tube and dried together with a 50-fold mole excess of modified nucleoside triphosphate in a centrifugal vacuum concentrator (Savant Speed Vac Concentrator). To this was added 30.0 ul of tdt reaction buffer (0.4M potassium cacodylate, 2 mM dithiothreitol, 16 mM magnesium chloride, at pH 7.1), 20.0 ul of a solution containing 500 ug bovine serum albumin per ml of water, 500 units of tdt, and sufficient water to bring the total volume to 75 ul. The reaction mixture was then allowed to incubate overnight in a 37 degree C. water bath. The total reaction time was typically 18 to 24 hours.

If the DNA was a homopolymer, the labeled product was separted from unreacted nucleoside triphosphate by binding the DNA to complementary homopolymer immobilized on cellulose particles (Pharmacia affinity purification media) at 10 degrees C. in 1N NaCl. 0.02N potassium phosphate, pH 7.5, followed by washing the cellulose at 20 degrees C. in the same buffer. "Tailed" homopolymers were then recovered by eluting the cellulose with water at 60–70 degrees C. If the DNA was not a homopolymer the separation was accomplished by gel permeation chromatography using Sephadex G-25 chomatography media (Pharmacia) and eluting in water or desired buffer.

C. Label Addition

The coupling of fluorophores of chemiluminescent compounds to the "tailed" oligomers was accomplished by adding amine-reactive derivatives of the labeling compounds to buffered solutions of the oligomers and allowing reactions to continue at room temperature overnight. The derivatized fluorophores were fluorescein-5-isothiocyanate, eosin-5-isothiocyanate, and N-hydroxysuccinimidyl 1-pyrenebutanoic acid. The chemiluminescent labeling compound was the N-hydroxysuccinimide (NHS) esters of 10-methylacridinium-9-(4-carboxyethylphenyl carboxylate) fluorosulfonate. Those skilled in the art will recognize that other amine reactive label moieties may be utilized as well. The derivatives were first dissolved in a non-interferring solvent (e.g. acetone, dimethyl sulfoxide, or dimethylformamide) at a concentration of 5–10 mM and then added dropwise to rapidly stirring oligomer solution. The NHS esters were generally added in several aliquots separated by 5 minutes each. The reaction buffers were 0.1M potassium phosphate, pH 8.0, for reactions involving NHS ester derivatives, and 0.05M sodium borate, pH 9.3, for reactions involving isothiocyanate derivatives. Labeled oligomers were isolated by either affinity chromatography or gel permeation chromatography as described above.

The phycobiliprotein, B-phycoerythrin, was conjugated to "tailed" oligomer using heterobifunctional crosslinking reagents. Maleimide groups were attached to the amine-modified oligomer by reacting 10 nmol of oligomer with 0.9 umol of succinimidyl 4-(maleimidomethyl) cyclohexane-1-carboxylate (SMCC). The SMCC was a 4.5 mM solution in ethanol and was added in nine separate additions, separated by five minutes each, to oligomer in 400 ul of 0.01N sodium phosphate, pH 5.0. The reaction was conducted at 30 degrees C. with stirring for a total reaction time of about 90 minutes. The product was isolated on a Sephadex G-25 chromatography column, eluted with water, and reduced in volume to approximately 500 ul in a centifugal vacuum concentrator.

Thiol groups were attached to B-phcoerythrin by reacting the protein with N-succinimidyl 3-(2-pyridyldithio) propionate (SPDP) followed by reductive cleavage of the disulfide. B-phycoerythrin (10 nmol) in ammonium sulfate suspension was first dialized overnight in 0.05N potassium phosphate, 0.05N NaCl, pH 7.5 buffer and isolated on a Sephadex G-25 column eluted with 0.01N potassium phosphate, 0.1N NaCl, pH 7.5.

The resulting solution was concentrated to about 1 ml using an Amicon PM-10 Ultrafiltration membrane and concentration cell. To this was added 0.15 umol of SPDP solution (2 mM SPDP in ethanol) and the reaction solution allowed to stir at room temperature for 80 minutes. The modified protein was recovered on a Sephadex G-25 column eluted with 0.1N sodium acetate, 0.1N NaCl, pH 4.5 buffer. Sufficient dithiothreitol was added to this solution to provide a final dithiothreitol concentration of 25 mM. The solution was allowed to stir at room temperature for about 1 hour at which time thiol-modified protein was isolated on a G-25 column eluted with 0.1N potassium phosphate, 1 mM EDTA, pH 7.0 buffer. The elution solution was immediately mixed with the maleimide derivatized oligomer, concentrated to about 500 ul on a centrifugal vacuum concentrator, and allowed to stir overnight at 4 degrees C. (approximately 24 hours). The reaction mixture was then fractionated on a Sephacryl S-200 column, eluted with 0.1N NaCl, 0.01N potassium phosphate, pH 7.5 buffer, and fractions combined which corresponded to a B-phycoerythrin absorbance eluting just prior to unconjugated B-phycoerythrin. The product was purified a second time using an immobilized homopolymer column as described above. The purified conjugate was stored at 4 degrees C.

D. Analysis of Labeled Oligomers

The composition of labeled oligomers was determined by absorbance spectroscopy. Absorbance spectra were recorded using a Cary 17D absorbance spectrophotometer (Varian Associates, Palo Alto, Calif.). Extinction coefficients for homopolymer absorbance were taken from the compilation of extinction coefficient data in the appendix section of the Pharmacia Molecular Biologicals catalog. Extinction coefficients of unconjugated fluorophores and chemiluminescent compounds were used in determining label concentrations in conjugated oligomer probes. The compositions of labeled oligomers prepared and analyzed by the above procedures are listed in Table I.

TABLE I

FLUORESCENT AND CHEMILUMINESCENT TAILED OLIGOMERS

| Oligo. | Tail Composition: Length | Base | Label Compound | Label Attached/ Olig. |
|---|---|---|---|---|
| $dT_{20}$ | 6.5 | AP-dCTP | pyrenebutanoic acid | 5.0 |
| $dT_{12}$ | 8.0 | AP-dCTP | eosin | 2.8 |
| $dT_{20}$ | 6.0 | AP-dCTP | fluorescein | 2.1 |
| $dT_{20}$ | 8.0 | AP-dCTP | ABEI | 4.8 |

TABLE I-continued
FLUORESCENT AND CHEMILUMINESCENT
TAILED OLIGOMERS

| Oligo. | Tail Composition: | | Label Compound | Label Attached/ Olig. |
|---|---|---|---|---|
| | Length | Base | | |
| $dT_{20}$ | 6.0 | AP-dCTP | acridinium ester | 4.7 |
| $dT_{20}$ | 6.5 | AP-dCTP | B-phycoerythrin | 0.5 |
| $dT_{20}$ | 1 | AP-ddCTP | pyrenebutanoic acid | 0.79 |
| $dA_{12}$ | 1 | AP-ddCTP | pyrenebutanoic acid | 0.54 |
| $dT_{12}$ | 1 | AP-ddCTP | pyrenebutanoic acid | 0.68 |
| $dT_{12}$ | 1 | AP-ddCTP | fluorescein | 1.0 |
| $dT_{12}$ | 1 | AP-ddCTP | fluorescein | 0.69 |

E. DNA Hybridizations Using Labeled Oligomers

Hybridizations using the B-phycoerythrin conjugate of dT20 (see Table I) were performed by the following blotting procedure. Nitrocellulose filter paper was pretreated by soaking in water followed by soaking in 6X SSC. The paper was then allowed to air dry. Target DNA, consisting of dA4000 for complementary target and dT3000 for noncomplementary target, was applied to the paper in separate spots, each spot representing a two-fold dilution of either target DNA. The paper was air dried and then baked at 80 degrees C. for 2 hours under vacuum. Prehybridization was performed by first soaking the filter paper in 6X SSC followed by soaking in a wetting solution comprised of 50 mM EDTA, 0.1% SDS, 1N NaCl, and 50 mM TRIS, at pH 8. The paper was then sealed in a plastic bag filled with 10 ml of prehybridization buffer, comprised of 5X Denhardt's, 5X SSC, 0.1% SDS, and 0.1 mg/ml tRNA. The nitrocellulose was allowed to soak in the buffer for 4 hours at which time the bag was drained and filled with 70 pmol of probe (based on dT20) in 1 ml of the same buffer. In another experiment, 130 pmol of probe was added to an identical blotted filter. Hybridization of probe to immobilized target was allowed to occur overnight at 4 degrees C. (approximately 16 hours). At the end of the hybridization period the filter was washed in 2X SSC containing 0.1% SDS at 4 degrees C. for several hours with three changes of the wash buffer. The nitrocellulose was air dried and prepared for front surface fluorescence measurements.

Hybridizations using the chemiluminescent acridinum ester conjugate of dT20 (see Table I) were performed in a similar manner as described above except that a Scleicher and Schuell (Keene, N.H.) Minifold II Slot Blotter was employed to immobilize DNA in slotted shaped blots instead of circular blots. The slot shape is more convenient to use with cuvettes in the luminometer while the circular blot used for the B-phycoerythrin conjugate was better matched by the defocussed excitation beam profile of the fluorometer. Prior to immobilizing target DNA the filter paper was soaked 3 times in water followed by soaking in 20X SET. The poly dT and poly dA targets were applied with the slot blot apparatus and air dried. The paper was then baked at 85 degrees C. for 2-4 hours under vacuum. Prehybridization of the nitrocellulose was performed by sealing the paper in plastic bags containing 1 ml of 6X SSC+5X Denhardt's reagent and allowing the paper to equilibrate for 3 hours at room temperature followed by soaking in another 1 ml of the same solution for an additional 90 minutes. The plastic bag was emptied of liquid and 1 pmol of probe added in 1 ml of the prehybridization buffer and the plastic bag sealed. Hybridization was allowed to occur overnight at 60 degrees C. (approximately 16 hours). At the end of this period the nitrocellulose paper was washed three times at 30 degrees C. in 4X SSC, fifteen minutes per wash. The filters were air dried and prepared for chemiluminescence measurements.

F. Detection of Fluorescent and Chemiluminescent Oligomers

Fluorescence of labeled oligomers was measured using an SLM 4800 spectrofluorometer (SLM-AMINCO Instruments, Urbana, Ill.) which was modified to allow photon counting detection. The modification consisted of using a Hamamatsu model R928 photomultiplier tube (Middlesex, N.J.) in a thermoelectric cooled housing (model TE-177RF, Products for Research, Danvers, Mass.), maintained near −30 degrees C., in place of the usual analog photomultiplier detector (also a Hamamatsu R928 photomultiplier tube). The photomultiplier tube anode current was amplified, conditioned, and counted using EG&G Ortec nuclear instrumentation modules (Oak Ridge, Tenn.) which included a model 9301 fast preamplifier, a model 9302 amplifier-discriminator, and a model 874 quad counter/timer. High voltage for the photomultiplier tube was provided with an EG&G Ortec model 478 power supply. Nitrocellulose filters were positioned in the fluorometer sample compartment using a mechanical assembly which positioned a filter at 45 degrees relative to both the path of the excitation light and the optical axis of the emission detector. Excitation of filters containing B-phycoerthrin labeled probe was performed at 500 nm with a 4nm monochromator bandpass. To reduce stray light interference, a 520 nm short pass interference filter (Ditric Optics, Hudson, Mass.) was placed in the excitation light path. Emission from the nitrocellulose was filtered through two Corning glass No. 3-66 long pass color filters (Corning Glass Works, Corning, N.Y.) and a Ditric 580 nm short pass interference filter. Due to the high level of background light detected (nitrocellulose filter fluorescence and scatter) a neutral density filter with O.D.=3 was also employed in the emission path.

Chemiluminescence measurements were made using a photon counting luminometer consisting of a light-tight sample compartment containing a cuvette holder and optics to collect the sample emission and focus it onto an RCA model 8850 photomultiplier tube (Lancaster, Penn.). The tube was powered with an EG&G Ortec model 456 power supply and was maintained at a temperature near −30 degrees C. in a Products for Research model TE-104RF thermoelectric cooled housing. The electronics for signal amplification, discrimination, and counting were identical to that described above for fluorescence measurements. The counter was interfaced to a Hewllett Packard model 9825 computer to allow acquisition of chemiluminescence data versus time in addition to data storage and processing. Nitrocellulose filter sections were cut to fit within a standard 1 cm path length cuvette and were held in position by a plastic insert. Chemiluminescence measurements of samples containing acridinium esters were initiated by automated injection of solution containing 0.1N NaOH and 8.8 nM hydrogen peroxide using a Hamilton Micro Lab P programmable liquid dispenser (Reno, Nev.). Filters were generally presoaked 2 minutes in 50 ul of 4X SSC adjusted to pH 3.0 to improve chemiluminescence yield.

The ability of the B-phcyoerythrin labeled probe to hybridize to complementary DNA was demonstrated using DNA "dot blots" on nitrocellulose filters. By visual examination of the nitrocellulose filters, under excitation using a hand-held ultraviolet light, B-phycoerythrin emission could be detected in blots containing as little as 5 ng of complementary $dA_{4000}$ target DNA. When probe was hybridized to corresponding blots containing $dT_{3000}$ (non-complementary target), no B-phycoerythrin emission was observed. Fluorescence intensities, measured using front surface fluorescence technique, were able to detect fluorescence to 1–2.5 ng $dA_{4000}$. The limitation in these measurements was the large background fluorescence emanating from the nitrocellulose filter material.

Figure 5:
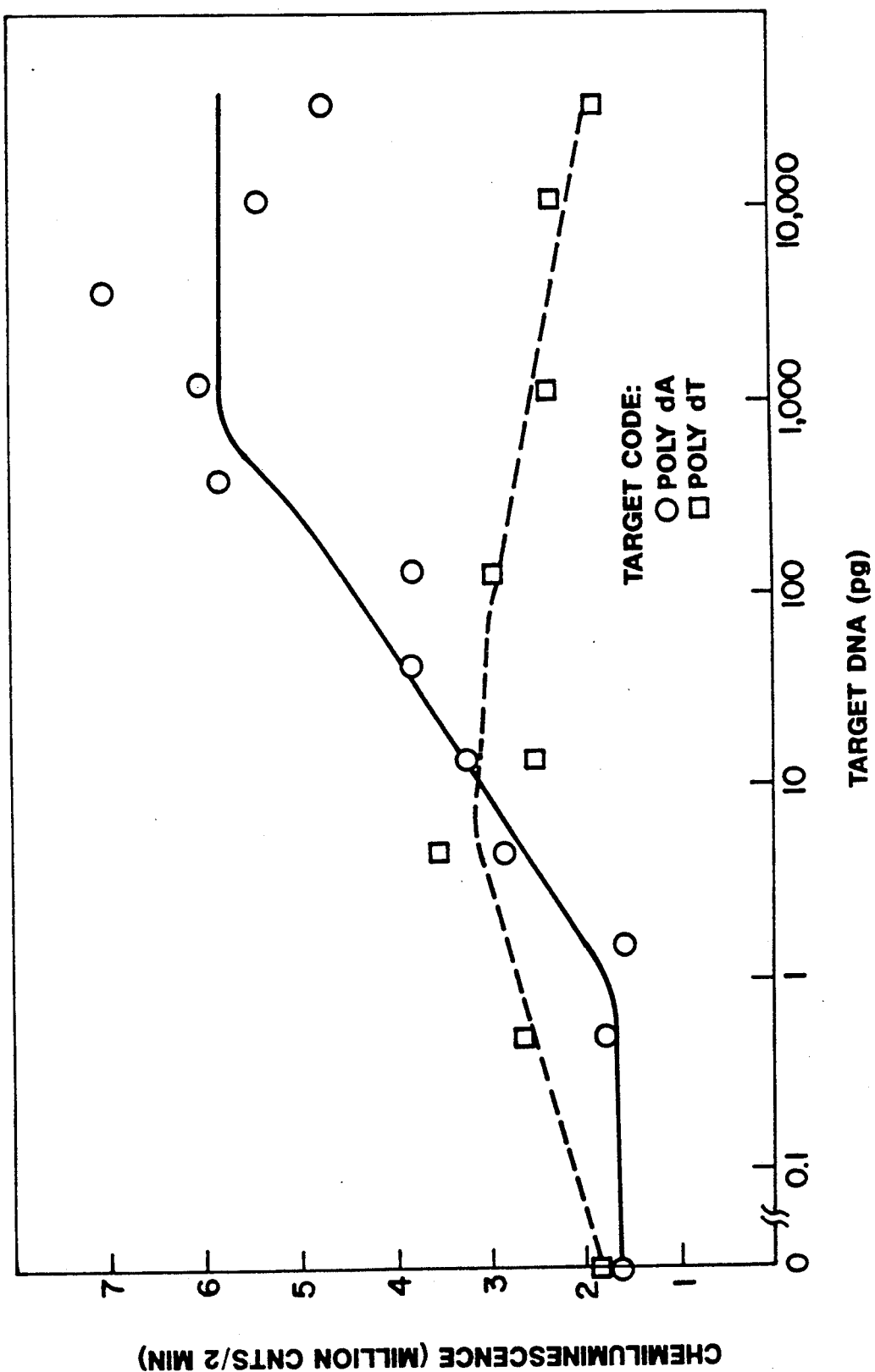

Detection of complementary DNA using an acridinium ester labeled probe was demonstrated using "slot blot" technique on nitrocellulose filters. The results of chemiluminescence measurements made on individual blots containing either complementary $dA_{4000}$ or non-complementary $dT_{3000}$ are plotted in FIG. 5. It may be seen from this figure that complementary target DNA (circles and solid line) may be distinguished from non-complementary DNA (square symbols and dashed line) at target DNA levels above about 100 pg.

The transamination method described herein for the conversion of nucleotide triphosphates into aliphatic-amine containing nucleotide triphosphates which are useful substrates for TdT is a concise and elegant method for labeling DNA. Major attractive features of the transamination reaction are 1) the reaction solvent is water 2) the reagents are relatively non-toxic and environmentally safe, and 3) the reaction is amenable to scale-up, factors which are all important in an industrial context. The preparation of the phosphoramidite is brief and high-yielding and the compound itself has proven to be useful in the strategic labeling of synthetic DNA oligomers.

Thus, while preferred embodiments of the invention have been described, the present invention is capable of variation and modification and, therefore, the invention should not be limited to the precise details set forth, but should include such changes and alterations as fall within the purview of the following claims.

What is claimed is:

1. A nucleotide having a linking group carried on an exocylic functional group of a nucleotide represented by the formula:

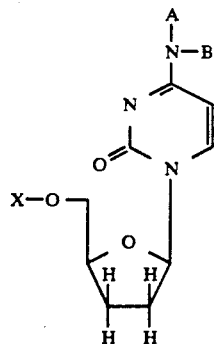

wherein X is hydrogen, mono, di, or triphoshate, or dimethoxytrityl; Z is hydrogen, hydroxyl, acetyl or a phosphoramidite, and A is represented by the formula:

—(CH$_2$)$_w$NHCOCK$_3$ wherein K is selected from the group of halogens consistently of Cl, Br, F, I and At and w is an integer from 3 to 9; and B is the same as A or hydrogen or A and B, taken together with the exocylic nitrogen, are

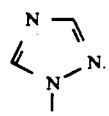

2. The compound of claim 1 wherein Z is (methyl-N, N-diisopropyl) phosphoramidite.

3. A nucleotide having a linking group carried on an exocyclic functional group of a nucleotide, represented by the formula:

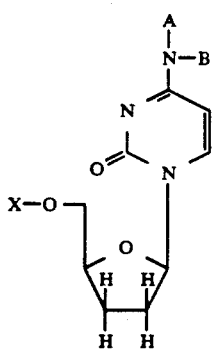

wherein X is hydrogen, mono, di, or triphosphate, or dimethoxytrityl; Z is a phosphoramidite; A is selected from the group consisting of the following:

—(CH$_2$)$_m$NH$_2$ wherein m is an integer from 1 to 9 and; B is the same as A or hydrogen.

4. The compound of claim 3 wherein said phosphoramidite is (methyl-N, N-diisopropyl) phosphoramidite.

* * * * *

UNITED STATES PATENT AND TRADEMARK OFFICE
CERTIFICATE OF CORRECTION

Page 1 of 3

PATENT NO. : 5,091,519
DATED : February 25, 1992
INVENTOR(S) : Kenneth Cruickshank It is certified that error appears in the above-indentified patent and that said Letters Patent is hereby corrected as shown below:

Column 2, line 32, "radio-labeled o-labeled" should read --radio--labeled--.

Column 3, lines 16 and 19, "without interferring" should read --without interfering--.

Column 4, line 48, "polymerase and other" should read --polymerase and others--.

Column 6, line 1, "further charactorized" should read --further characterized--.

Column 6, line 7, "(D$_2$O)" should read --(D$_2$O--.

Column 6, line 42, "and an the appropriate time" should read --and at the appropriate time--.

Column 7, line 11, "fore-going" should read --foregoing--.

Column 7, line 22, "descried" should read --described--.

Column 7, line 43, "NcHCO$_3$" should read --NaHCO$_3$--.

Column 7, line 46, "(3.5g, 41%)" should read --3.5g (41%)--.

Column 8, line 5, "iisopropyl)" should read --diisopropyl--.

Column 8, line 66, "to sequentially attached" should read --to sequentially attach--.

Column 9, line 24, "was separted" should read --was separated--.

Column 9, line 27, "NaCl." should read --NaCl,--

Column 9, line 34, "G-25 chomatography" should read --G-25 chromatography--.

UNITED STATES PATENT AND TRADEMARK OFFICE
CERTIFICATE OF CORRECTION

PATENT NO. : 5,091,519
DATED : February 25, 1992
INVENTOR(S) : Kenneth Cruickshank It is certified that error appears in the above-indentified patent and that said Letters Patent is hereby corrected as shown below:

Column 9, line 47, "esters" should read --ester--.

Colunm 9, line 51, "non-interferring" should read --non-interfering--.

Column 10, line 9, "centifugal vacuum" should read --centrifugal vacuum--.

Column 10, line 18, "B-phcoerythrin" should read --B-phycoerythrin--.

Column 11, line 31, "Denhardt's" should read --Denhardt's reagent--.

Column 13, line 1, "B-phcyoerythrin" should read --B-phycoerythrin--.

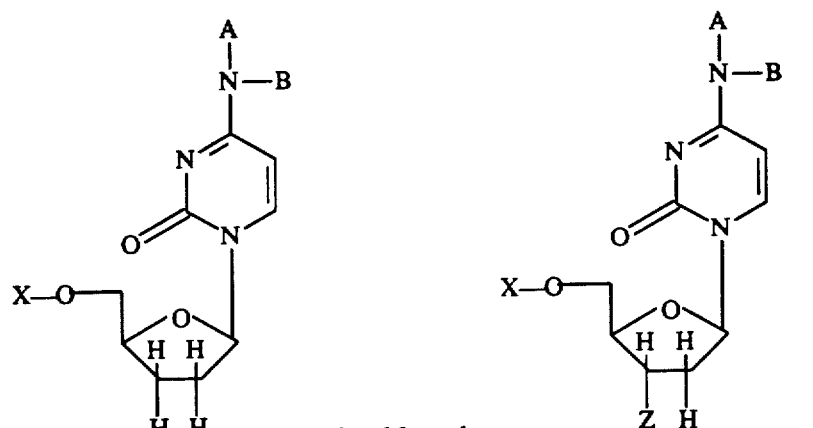

Colunm 14, line 15, "                    " should read --                    --

Column 14, lines 23-24, "consistently" should read --consisting--.

UNITED STATES PATENT AND TRADEMARK OFFICE
CERTIFICATE OF CORRECTION

PATENT NO. : 5,091,519

DATED : February 25, 1992

INVENTOR(S) : Kenneth Cruickshank

It is certified that error appears in the above-indentified patent and that said Letters Patent is hereby corrected as shown below:

Colunm 14, line 54, " 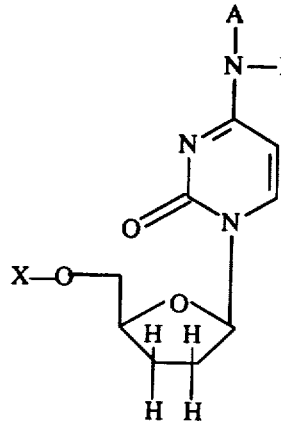 " should read -- 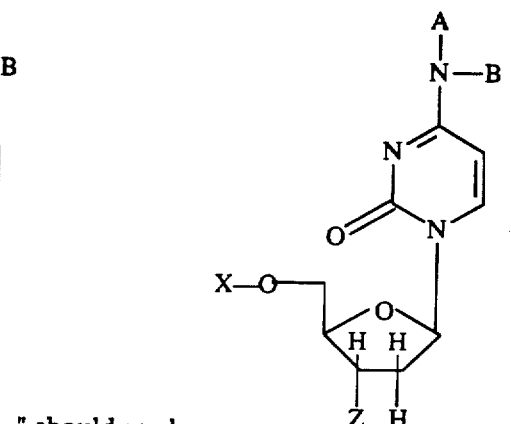 --

Signed and Sealed this

Twenty-third Day of November, 1993

*Attest:*

BRUCE LEHMAN

*Attesting Officer*  *Commissioner of Patents and Trademarks*